(12) United States Patent
Maldonado

(10) Patent No.: US 10,487,199 B2
(45) Date of Patent: Nov. 26, 2019

(54) ACTIVATED FILMS HAVING LOW SOUND PRESSURE LEVELS

(71) Applicant: The Procter & Gamble Company, Cincinnati, OH (US)

(72) Inventor: Clarissa Maldonado, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 949 days.

(21) Appl. No.: 14/664,974

(22) Filed: Mar. 23, 2015

(65) Prior Publication Data

US 2015/0376384 A1 Dec. 31, 2015

Related U.S. Application Data

(60) Provisional application No. 62/017,576, filed on Jun. 26, 2014.

(51) Int. Cl.
*A61F 13/514* (2006.01)
*A61F 13/551* (2006.01)
(Continued)

(52) U.S. Cl.
CPC ............ *C08L 23/06* (2013.01); *A61F 13/514* (2013.01); *A61F 13/51401* (2013.01); *A61F 13/51456* (2013.01); *A61F 13/51462* (2013.01); *A61F 13/51464* (2013.01); *A61F 13/551* (2013.01); *A61L 15/00* (2013.01); *A61L 15/225* (2013.01);
(Continued)

(58) Field of Classification Search
CPC .. A61L 15/42; A61F 13/514; A61F 13/51401; A61F 13/51456; A61F 13/51462; A61F 13/51464; A61F 13/551; C08J 5/18; C08K 2003/2237; C08K 2003/265; C08K 3/26

See application file for complete search history.

(56) References Cited

U.S. PATENT DOCUMENTS 3,563,243 A 2/1971 Lindquist
3,860,003 A 1/1975 Buell
(Continued)

FOREIGN PATENT DOCUMENTS

CN 1300305 A 6/2001
EP 0194150 9/1986
(Continued)

OTHER PUBLICATIONS

Vasile, Handbook of Polyolefins, Chapter 16, 200, Marcel Dekker, Inc., Second Edition, pp. 401-411. (Year: 2000).*

(Continued)

*Primary Examiner* — Peter S Vasat
(74) *Attorney, Agent, or Firm* — Daniel S. Albrecht; Wednesday G. Shipp

(57) ABSTRACT

A film comprising from about 20 wt. % to about 85 wt. % of a polyolefin component and from about 20 wt. % to about 45 wt. % of a particle component; wherein the film has a basis weight of from about 5 gsm to about 25 gsm; wherein the film is activated and subjected to an engineering strain of greater than about 20%; wherein the film has a predicted sound pressure level over the frequency octave range of 2000 Hz-6300 Hz of less than about 43 dB.

23 Claims, 3 Drawing Sheets

(51) Int. Cl.

| | | |
|---|---|---|
| *C08J 5/18* | (2006.01) | |
| *A61L 15/42* | (2006.01) | |
| *A61F 13/15* | (2006.01) | |
| *C08L 23/06* | (2006.01) | |
| *A61L 15/22* | (2006.01) | |
| *C08K 3/22* | (2006.01) | |
| *C08K 3/26* | (2006.01) | |
| *A61L 15/54* | (2006.01) | |
| *A61L 15/00* | (2006.01) | |

(52) U.S. Cl.
CPC ............ *A61L 15/42* (2013.01); *A61L 15/54* (2013.01); *C08J 5/18* (2013.01); *C08K 3/22* (2013.01); *C08K 3/26* (2013.01); *A61F 13/15* (2013.01); *C08J 2323/04* (2013.01); *C08J 2423/14* (2013.01); *C08K 2003/2237* (2013.01); *C08K 2003/265* (2013.01)

(56) References Cited

U.S. PATENT DOCUMENTS

| | | | |
|---|---|---|---|
| 3,911,173 | A | 10/1975 | Sprague, Jr. |
| 3,929,135 | A | 12/1975 | Thompson |
| 4,324,246 | A | 4/1982 | Mullane et al. |
| 4,342,314 | A | 8/1982 | Radel et al. |
| 4,463,045 | A | 7/1984 | Ahr et al. |
| 4,472,328 | A | 9/1984 | Sugimoto et al. |
| 4,554,297 | A | 11/1985 | Dabi |
| 4,573,986 | A | 3/1986 | Minetola et al. |
| 4,609,518 | A | 9/1986 | Curro et al. |
| 4,610,678 | A | 9/1986 | Weisman et al. |
| 4,629,643 | A | 12/1986 | Curro et al. |
| 4,636,207 | A | 1/1987 | Buell |
| 4,673,402 | A | 6/1987 | Weisman et al. |
| 4,695,278 | A | 9/1987 | Lawson |
| 4,704,115 | A | 11/1987 | Buell |
| 4,740,520 | A | 4/1988 | Hallenbach et al. |
| 4,785,996 | A | 11/1988 | Ziecker et al. |
| 4,795,454 | A | 1/1989 | Dragoo |
| 4,798,602 | A * | 1/1989 | Laus ................. A61F 13/51464 428/500 |
| 4,808,178 | A | 2/1989 | Aziz et al. |
| 4,834,735 | A | 5/1989 | Alemany et al. |
| 4,842,666 | A | 6/1989 | Werenicz |
| 4,888,231 | A | 12/1989 | Angstadt |
| 4,892,536 | A | 1/1990 | Desmarais et al. |
| 4,900,317 | A | 2/1990 | Buell |
| 4,902,553 | A | 2/1990 | Hwang et al. |
| 4,909,803 | A | 3/1990 | Aziz et al. |
| 4,940,464 | A | 7/1990 | VanGompel et al. |
| 4,950,254 | A | 8/1990 | Andersen et al. |
| 4,988,344 | A | 1/1991 | Reising et al. |
| 4,988,345 | A | 1/1991 | Reising et al. |
| 4,990,147 | A | 2/1991 | Freeland et al. |
| 5,006,394 | A | 4/1991 | Baird |
| 5,037,416 | A | 8/1991 | Allen et al. |
| 5,085,654 | A | 2/1992 | Buell |
| 5,092,861 | A | 3/1992 | Nomura et al. |
| 5,147,345 | A | 9/1992 | Young et al. |
| 5,200,247 | A | 4/1993 | Wu et al. |
| 5,234,423 | A | 8/1993 | Alemany et al. |
| 5,246,433 | A | 9/1993 | Hasse et al. |
| 5,260,345 | A | 11/1993 | Desmarais et al. |
| 5,269,775 | A | 12/1993 | Freeland et al. |
| 5,342,338 | A | 8/1994 | Roe |
| RE34,920 | E | 4/1995 | Aziz et al. |
| 5,407,979 | A | 4/1995 | Wu et al. |
| 5,445,862 | A * | 8/1995 | Kaneko ................. C08J 5/18 428/148 |
| 5,492,751 | A | 2/1996 | Butt, Sr. et al. |
| 5,507,760 | A | 4/1996 | Wynne et al. |
| 5,569,234 | A | 10/1996 | Buell et al. |
| H1630 | H | 1/1997 | Roe |
| 5,607,760 | A | 3/1997 | Roe |
| 5,609,587 | A | 3/1997 | Roe |
| 5,628,097 | A | 5/1997 | Benson et al. |
| 5,635,191 | A | 6/1997 | Roe et al. |
| 5,637,105 | A | 6/1997 | Tanaka et al. |
| H1670 | H | 7/1997 | Aziz et al. |
| 5,643,588 | A | 7/1997 | Roe et al. |
| 5,769,838 | A | 6/1998 | Buell et al. |
| 5,897,545 | A | 4/1999 | Kline et al. |
| 5,899,895 | A | 5/1999 | Roles et al. |
| 5,899,896 | A | 5/1999 | Suprise et al. |
| 5,916,661 | A | 6/1999 | Benson et al. |
| 5,941,864 | A | 8/1999 | Roe |
| 5,957,908 | A | 9/1999 | Kline et al. |
| 5,968,025 | A | 10/1999 | Roe et al. |
| 6,013,151 | A | 1/2000 | Wu et al. |
| 6,107,539 | A | 8/2000 | Palumbo et al. |
| 6,118,041 | A | 9/2000 | Roe et al. |
| 6,120,487 | A | 9/2000 | Ashton |
| 6,120,489 | A | 9/2000 | Johnson et al. |
| 6,156,421 | A * | 12/2000 | Stopper ................. B32B 5/22 428/315.5 |
| 6,414,215 | B1 | 7/2002 | Roe |
| 6,476,288 | B1 | 11/2002 | Graves et al. |
| 6,545,197 | B1 | 4/2003 | Muller et al. |
| 6,627,787 | B1 | 9/2003 | Roe et al. |
| 6,680,422 | B2 | 1/2004 | Roe |
| 6,953,510 | B1 | 10/2005 | Mackay et al. |
| 7,270,723 | B2 * | 9/2007 | McCormack ....... B32B 38/0032 156/229 |
| 8,937,211 | B2 | 1/2015 | Dent et al. |
| 2002/0017376 | A1 | 2/2002 | Geltser et al. |
| 2003/0047271 | A1 | 3/2003 | Wu et al. |
| 2003/0233082 | A1 | 12/2003 | Kline et al. |
| 2005/0112338 | A1 | 5/2005 | Faulks et al. |
| 2005/0215963 | A1* | 9/2005 | Autran ............. A61F 13/15203 604/358 |
| 2012/0034837 | A1 | 2/2012 | Ngai et al. |

FOREIGN PATENT DOCUMENTS

| | | |
|---|---|---|
| WO | WO 95/24173 A2 | 9/1995 |
| WO | WO 00/69382 A1 | 11/2000 |

OTHER PUBLICATIONS

International Search Report, PCT/US2015/037360, dated Oct. 9, 2015, 10 pages.

Vasile, Handbook of Polyolefins, Chapter 16, 2000, Marcel Dekker, Inc., Second Edition, pp. 401-411.

* cited by examiner

ACTIVATED FILMS HAVING LOW SOUND PRESSURE LEVELS

FIELD OF THE INVENTION

The present invention relates to a film comprising a polyolefin component and a particle component. The film has a basis weight of from about 5 gsm to about 25 gsm. The film is activated and subjected to an engineering strain of greater than about 20%. The film has a sound pressure level of less than about 43 dB as determined by the Sound Pressure Level Test herein.

BACKGROUND OF THE INVENTION

Films are commonly used as barriers. Some films are engineered to be liquid impervious and moisture impervious such as those used as protective packages or those used in absorbent products. Other films are engineered to be liquid impervious and moisture permeable such as those used in diapers or adult incontinence products.

In some instances, it may be desirable for the product or package to not produce a lot of noises. It is desirable for products such as feminine pads, incontinence products, tampons, and their packaging to be discrete, therefore it is preferred that these products and packages generate the lowest amount of noise possible. Other products like diapers and premium packages seek to mimic the appearance and feel of cloth, therefore plastic sounding materials are less desirable.

Sound is the result of a vibrating object pushing the air surrounding it and creating bands of high and low pressure. These bands of high and low pressure are longitudinal waves that the human ear perceives as sound. Each sound can be described by a magnitude, known as sound pressure level measured in decibels (dB) and a frequency which is measured in hertz (Hz). The human auditory system is most sensitive from 2,000 to 5,000 Hz due to the resonance of the ear canal. An object vibrates as a result of an input force of a certain magnitude and frequency and the mass, stiffness and damping characteristics of the object. One way to reduce the noise generated by a product containing a film is to reduce the noise produced by the film. This can be achieved by reducing the film stiffness, increasing its mass or changing its damping characteristics.

The stiffness of an elastic film is calculated using the Young's modulus E of the film. The Young's modulus is the slope of the stress strain curve at the strains of interest. Typically, films are anisotropic, therefore they will have different Young's modulus depending on the tensile test direction. The speed at which the tensile test is conducted will also impact the resulting modulus. The measurements should be taken at speeds relevant to the application.

The strain levels that vibrating thin polyolefin films experience are small and in most cases below the yield point of the film. Therefore the strains considered when calculating Young's modulus are between 0.01 and 0.05.

The extrusion and processing conditions under which a film is produced will impact the level of crystallization on the film which in turn will affect the resulting modulus and noise produced by the film. For example, in cast extrusion processes the temperature of the casting roll, chill rolls temperatures and arrangements, melt temperature, take off-speed and annealing roll temperature will affect the level of crystallization on the film and may impact the film stiffness and noise.

Polymer structures can be anywhere from 5% to 95% crystalline. In addition to extrusion processing conditions, the level of crystallinity will also depend on the simplicity of the chain structure, chemistry, side branching and whether the polymer is isotactic, syndiotactic or atactic. Some of the known methods used to measure the amount of crystallinity in a polymer make use of Differential Scanning calorimetry, X-Ray Diffraction or by a density measurement if the density of the crystal phase and amorphous phases are known. The more crystalline the polymer structure, the higher the Young's modulus and the noise produced by the resulting film. For example: Resin blends with higher content of resins with higher side branching such as Low Density Polyethylene are preferred as their typical degree of crystallinity is 45-55%. Less content of polymers with chain regularity is preferred such as isotactic polypropylene which typical degree of crystallinity is 70%-80%.

Incremental stretching of thermoplastic film typically involves running the film between grooved or toothed rollers. The grooves or teeth on the rollers intermesh and stretch the film as the film passes between the rollers. Incremental stretch can stretch a film in many small increments that are evenly spaced across the film. The depth at which the intermeshing teeth engage can control the degree of stretching. One type of incremental stretching is referred to as ring-rolling.

Therefore, it is an object of the present invention to produce films that have a sound pressure level of less than about 43 dB as determined by the Sound Pressure Level Test herein.

SUMMARY OF THE INVENTION

The present invention is directed to a film comprising from about 20 wt. % to about 85 wt. % of a polyolefin component and from about 20 wt. % to about 45 wt. % of a particle component. The film of the present invention has a basis weight of from about 5 gsm to about 25 gsm prior to activation. The film is activated and subjected to an engineering strain of greater than about 20%. The film of the present invention has a sound pressure level of less than about 43 dB as determined by the Sound Pressure Level Test herein. Optionally, the film may comprise from about 1 wt. % to about 30 wt. % of an elastomeric resin. The film of the present invention may be used in absorbent articles and/or packages and/or wrappers.

DETAILED DESCRIPTION OF THE INVENTION

Figure 1:
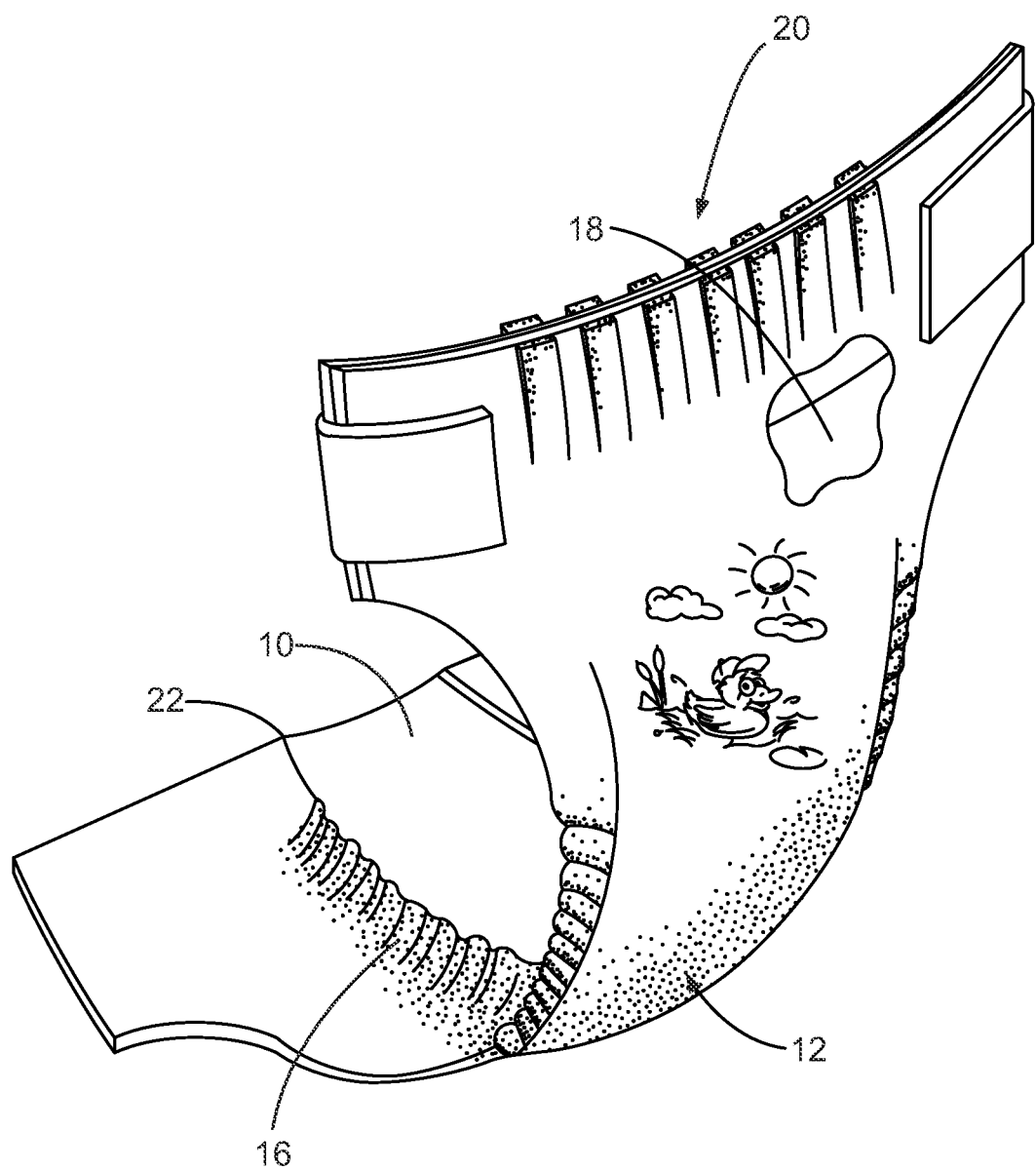
FIG. 1 is a perspective view of an absorbent article made according to the present invention.

As used herein, the following terms have the following meanings:

As used herein, the term "absorbent articles" refers to devices that absorb and contain body exudates, and, more specifically, refers to devices that are placed against or in proximity to the body of the wearer to absorb and contain the various exudates discharged from the body. Absorbent articles may include diapers, pants, training pants, an absorbent insert for a diaper or pant, adult incontinence undergarments, feminine hygiene products such as a sanitary napkin and a pantiliner, breast pads, care mats, bibs, wound dressing products, and the like. As used herein, the term "body fluids" or "body exudates" includes, but is not limited to, urine, blood, vaginal discharges, breast milk, sweat and fecal matter.

As used herein, the term "absorbent core" refers to the component of the absorbent article that is primarily responsible for fluid handling properties of the article, including acquiring, transporting, distributing and storing body fluids. As such, the absorbent core typically does not include the topsheet, backsheet or outer cover of the absorbent article.

As used herein, the term "bonded" refers to different materials being attached (cohesively or adhesively) in at least a portion thereof. The attached portions may be random or may have a pattern such as stripes, spirals, dots, and the like. The attached portions may be located at the peripheries, throughout the surface area, or both. Suitable attachment means known in the art may be used, including but not limited to adhesives, heat, pressure, crimping, ultrasonic, chemical (via hydrogen bonds or other cohesive forces), mechanical (e.g., fasteners, entanglements), hydraulic, vacuum and combinations thereof.

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

As used herein, the term "disposable" is used in its ordinary sense to mean an article that is disposed or discarded after a limited number of usage events over varying lengths of time, preferably less than about 20 events, more preferably less than about 10 events, even more preferably less than about 5 events, and most preferably less than about 2 events.

As used herein, the term "joined" encompasses configurations wherein an element is directly secured to the other element by affixing the element directly to the other element, and configurations wherein the element is indirectly secured to the other element by affixing the element to intermediate member(s), which in turn are affixed to the other element.

The term "longitudinal" refers to a direction running from a waist edge to an opposing waist edge of the article and generally parallel to the maximum linear dimension of the article. Directions within ±45° of the longitudinal direction are considered to be "longitudinal".

The term "lateral" refers to a direction running from a side edge to an opposing side edge of the article and generally at a right angle to the longitudinal direction and in the same plane as the longitudinal direction. Directions within ±45° of the lateral direction are considered to be "lateral".

As used herein, the term "nonwoven" refers to a web that has a structure of individual fibers which are interlaid forming a matrix, but not in an identifiable repeating manner. Nonwoven webs may be formed by a variety of processes known to those skilled in the art, for example, meltblowing, spunbonding, wet-laying, air-laying, and various bonding-carding processes.

The terms "pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers", "prefastened diapers", "pull-on diapers", "training pants" and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

As used herein, the term "region" refers to a zone or an area comprising a material being physically, chemically, or visually distinguishable from surrounding or adjoining materials. Various regions of materials may include transitional regions in between. The regions may be positioned in the z-dimension or in the xy-dimension. As used herein, the term "z-dimension" refers to the dimension orthogonal to the length and width of the structure or article. The z-dimension usually corresponds to the thickness of the structure or article. As used herein, the term "xy-dimension" refers to the plane orthogonal to the thickness of the member, core or article when the member, core or article is in a flat-out state. The xy-dimension usually corresponds to the length and width, respectively, of the structure or article in a flat-out state.

The films of the present invention may have a basis weight of from about 5 gsm to about 25 gsm; from about 15 gsm to about 25 gsm; from about 13 gsm to about 15 gsm; from about 12 gsm to about 14 gsm; from about 11 gsm to about 13 gsm; from about 8 gsm to about 12 gsm; less than about 25 gsm; less than about 20 gsm; less than about 15 gsm; greater than about 5 gsm; greater than about 8 gsm; greater than about 10 gsm. Basis weight measurements are made prior to activation.

The films of the present invention may comprise from about 20 wt. % to about 80 wt. % of a polyolefin component. The polyolefin component may be selected from the group consisting of linear low density polyethylene polymers, low density polyethylene polymers, high density polyethylene polymers, polypropylene polymers, linear medium density polyethylene polymers, and mixtures thereof. Developments towards optimization of production processes of polyolefin resins may result in variants of the polyolefin versions mentioned in this group, which may also be suitable for this application. The polyolefin component may have a density of from about 0.91 g/cm3 to about 0.95 g/cm3.

The polyolefin component may be any of the class of thermoplastic polyolefin polymers or copolymers that are processable into a film or for direct lamination by melt extrusion onto the fibrous web. A number of thermoplastic polymers suitable in the practice of the invention are olefin based polymers including the most common ethylene or propylene based polymers such as polyethylene, polypropylene, and copolymers such as ethylene vinylacetate (EVA), ethylene methyl acrylate (EMA) and ethylene acrylic acid (EAA), or blends of such polyolefins.

The particle component may be present in an amount of from about 20 wt. % to about 50 wt. %; from about 35 wt. % to about 45 wt. %; from about 30 wt. % to about 40 wt. %; from about 25 wt. % to about 35 wt. %; from about 25 wt. % to about 40 wt. %; less than about 50 wt. %; less than about 45 wt. %; less than about 40 wt. %; greater than about 20 wt. %; greater than about 25 wt. %; greater than about 30 wt. % of the film.

The particle component may be selected from the group consisting of friction reducing particles and opacifier particles. The particle component may be selected from the group consisting of $CaCO_3$, $TiO_2$, and combinations thereof. The particle component may have a density of from about 1.8 g/cm3 to about 4.5 g/cm3. The particle component may have a density of at least about 2 times the density of the polyolefin component. Other particles may be used as friction reducing particles, pigments, opacifiers or to provide other benefits. Some examples are clays, silica, alumina, barium sulfate, sodium carbonate, talc, magnesium sulfate, zeolites, aluminum sulfate, diatomaceous earth, magnesium carbonate, barium carbonate, kaolin, mica, carbon, calcium oxide, magnesium oxide and aluminum hydroxide.

The film may be achieved by formulating a thermoplastic polymer with suitable additives and pore-forming fillers to provide an extrudate or film for embossing and lamination with the nonwoven web. $CaCO_3$ is a common filler. Microporous-formable compositions of polyolefins, inorganic or organic pore-forming fillers and other additives to make microporous sheet materials are known. This method may be done in line and provides economies in manufacturing and/or materials over known methods of making laminates. In addition, as developed above, microporous-formable polymer compositions may be obtained from blends of polymers such as a blend of an alkanoyl polymer and polyvinyl alcohol as described in U.S. Pat. No. 5,200,247. In addition, blends of an alkanoyl polymer, destructured starch and an ethylene copolymer may be used as the microporous-formable polymer composition as described in U.S. Pat. No. 5,407,979. With these polymer blends, it is unnecessary to use pore-forming fillers to provide microporosity upon incremental stretching. Rather, the different polymer phases in the film themselves, when the film is stretched at ambient or room temperature, produce microvoids.

The films of the present invention may be activated and subjected to an engineering strain of greater than about 15%; greater than about 20%. The film may be subjected to an engineering strain of from about 20% to about 70%. The film may be activated with a 1.52 mm pitch tooling such that the depth of engagement of the tooling is from about 0.508 mm to about 1.27 mm.

The films of the present invention may comprise an elastomeric resin. The elastomeric resin may be present in an amount of from about 1 wt. % to about 30 wt. %; from about 5 wt. % to about 30 wt. %; from about 25 wt. % to about 35 wt. %; from about 15 wt. % to about 20 wt. %; from about 15 wt. % to about 18 wt. %; from about 10 wt. % to about 15 wt. % from about 5 wt. % to about 10 wt. %; less than about 35 wt. %; less than about 30 wt. %; less than about 25 wt. %; less than about 20 wt. %; greater than about 1 wt. %; greater than about 5 wt. %; greater than about 10 wt. %; greater than about 15 wt. % by weight of the film. The elastomeric resin may be selected from the group consisting of propylene based elastomer, propylene ethylene copolymer, styrenic block copolymer resin. Some examples are poly(ethylene-butene), poly(ethylene-hexene), poly(ethylene-octene), poly(ethylene-propylene), poly(styrene-butadiene-styrene), poly(styrene-isoprene-styrene), poly(styrene-ethylene-butylene-styrene), poly(ester-ether), poly(ether-amide), poly(ethylene-vinylacetate), poly(ethylene-methylacrylate), poly(ethylene-acrylic acid), poly(ethylene butylacrylate), polyurethane, poly(ethylene-propylene-diene), ethylene-propylene rubber and mixtures thereof. The elastomeric resin may have a degree of crystallinity or end block content of from about 5% to about 30%.

Thermal stabilizers, UV stabilizers, antioxidants, antiblocking, lubricants, anti-static and slip agents and other additives may be added to the formula to improve the stability of the film when exposed to UV light, oxidizing agents, high temperatures and/or to aid in the production or processing of the resulting film. Examples of such additives include but are not limited to fatty amines, phenolic and phosphite antioxidant additives.

Films suitable for the present invention may be breathable films. Breathable films are polymeric films containing filler stretched to contain internal microporosities. Breathable films are described in U.S. Pat. No. 4,472,328

The films of the present invention may be useful in packaging films. Further, the films of the present invention may be useful in absorbent articles or a component of an absorbent article such as a backsheet, waistband, fastening members, and ears.

FIG. 1 depicts the absorbent articles of the present invention, e.g., diaper(s) 20, which comprise a liquid pervious topsheet 10, a backsheet 12 that is at least partially joined to the topsheet 10, an absorbent core 18 disposed at least partially between the topsheet 10 and the backsheet 12, a first cuff 16 along a longitudinal edge 22 of the topsheet 10. In certain embodiments, the absorbent articles may additionally include one or more components selected from the group consisting of an outer cover, side panels, an elastic feature, a fastening system, and combinations thereof.

An outer cover (which may comprise the backsheet) forms the chassis, onto which other components of the diaper are added to form the unitary structure of the diaper. In alternative embodiments, the article may be preformed by the manufacturer to create a pant. The term "pant", as used herein, refers to disposable garments having a waist opening and leg openings designed for infant or adult wearers. A pant may be placed in position on the wearer by inserting the wearer's legs into the leg openings and sliding the pant into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). While the term "pant" is used herein, pants are also commonly referred to as "closed diapers", "prefastened diapers", "pull-on diapers", "training pants" and "diaper-pants". Suitable pants are disclosed in U.S. Pat. Nos. 5,246,433; 5,569,234, 6,120,487, 6,120,489, 4,940,464, 5,092,861, 5,897,545, 5,957,908, and U.S. Patent Publication 2003/0233082A1.

The absorbent articles of the present invention comprise a topsheet 10. The topsheet is preferably compliant, soft feeling, and non-irritating to the wearer's skin. It can be elastically stretchable in one or two directions. The topsheet has at least one longitudinal edge 22 and in most instances has two. Further, the topsheet is liquid pervious, permitting liquids (e.g., menses, urine, and/or runny feces) to readily penetrate through its thickness. A suitable topsheet can be manufactured from a wide range of materials such as woven and nonwoven materials; apertured or hydroformed thermoplastic films; porous foams; reticulated foams; reticulated thermoplastic films; and thermoplastic scrims. Suitable woven and nonwoven materials may comprise of natural fibers such as wood or cotton fibers; synthetic fibers such as polyester, polypropylene, or polyethylene fibers; or combinations thereof. If the topsheet includes fibers, the fibers may be spunbond, carded, wet-laid, meltblown, hydroentangled, or otherwise processed as is known in the art. One suitable topsheet comprising a web of staple-length polypropylene fibers is manufactured by Veratec, Inc., a Division of International Paper Company, of Walpole, Mass. under the designation P-8.

Preferred topsheet for use in the present invention are selected from high loft nonwoven topsheets and apertured film topsheet. Apertured film topsheet typically are pervious to bodily exudates, yet non-absorbent, and have a reduced tendency to allow fluids to pass back through and rewet the wearer's skin. Suitable apertured films include those described in U.S. Pat. Nos. 5,628,097, 5,916,661, 6,545,197, 6,107,539, and PCT Patent Publication WO 00/69382 A2.

Further, suitable topsheet materials for depositing solid excretions thereon may include nonwovens having apertures, which are at least in the portions that are aligned with the feces deposition region of the article. Suitable apertured nonwovens are described in more detail in U.S. Pat. Nos. 6,414,215, 5,342,338, and 5,941,864 and U.S. Patent Publication 2002/017376. In another embodiment of feces handling articles, such topsheets can be combined with feces handling members, e.g., underlying such topsheets, and which are further described in the abovementioned patent documents.

Suitable formed film topsheets are described in U.S. Pat. Nos. 3,929,135, 4,324,246, 4,342,314, 4,463,045, 5,006, 394. Other suitable topsheets may be made in accordance with U.S. Pat. Nos. 4,609,518 and 4,629,643. Such formed films are available from The Procter & Gamble Company of Cincinnati, Ohio as "DRI-WEAVE" and from Tredegar Corporation, based in Richmond, Va., as "CLIFF-T."

Preferably, at least a portion of the topsheet is made of a hydrophobic material or is treated to be hydrophobic in order to isolate the wearer's skin from liquids contained in the absorbent core. If the topsheet is made of a hydrophobic material, preferably at least a portion of the upper surface of the topsheet is treated to be hydrophilic so that liquids will transfer through the topsheet more rapidly. The topsheet can be rendered hydrophilic by treating it with a surfactant or by incorporating a surfactant into the topsheet. Suitable methods for treating the topsheet with a surfactant include spraying the topsheet material with the surfactant and/or immersing the material into the surfactant. A more detailed discussion of such a treatment and hydrophilicity is contained in U.S. Pat. Nos. 4,988,344, 4,988,345, and 4,950, 254. A more detailed discussion of some suitable methods for incorporating a surfactant in the topsheet 24 can be found in U.S. Statutory Invention Registration No. H1670. Alternatively, the topsheet may include an apertured web or film which is hydrophobic. This may be accomplished by eliminating the hydrophilizing treatment step from the production process and/or applying a hydrophobic treatment to the topsheet, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet may be coated with a lotion as is known in the art. Examples of suitable lotions include those described in U.S. Pat. Nos. 5,607,760, 5,609,587, 5,635,191, 5,643,588, and 5,9680,25. The lotion may function alone or in combination with another agent as the hydrophobizing treatment described above. The topsheet may also include or be treated with antibacterial agents, some examples of which are disclosed in PCT Publication No. WO 95/24173. Further, the topsheet, the outer cover or any portion of the topsheet or outer cover may be embossed and/or matte finished to provide a more cloth like appearance.

The topsheet may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" (from the article) is increased. Typically, the aperture should have an area of between about 10 cm$^2$ and about 50 cm$^2$. The aperture preferably has an area of between about 15 cm$^2$ and 35 cm$^2$.

Further, the topsheet may be fully or partially elasticated or may be foreshortened so as to provide a void space between the topsheet and the core. Exemplary structures including elasticized or foreshortened topsheets are described in more detail in U.S. Pat. Nos. 4,892,536, 4,990, 147, 5,037,416, and 5,269,775.

The absorbent article further comprises a first cuff 16 along a longitudinal edge 22 of the topsheet 10. This first cuff 16 is useful for providing improved containment of liquids and other body exudates. First cuffs 16 may also be referred to as outer leg cuff, leg bands, side flaps, leg cuffs or elasticized cuffs. U.S. Pat. No. 3,860,003 describes a disposable diaper which provides a contractible leg opening having a side flap and one or more elastic members to provide an elasticized leg cuff.

The first cuff 16 may be constructed in a number of different configurations, including those described in U.S. Pat. Nos. 3,860,003, 4,636,207, 4,695,278, 4,704,115, 4,795,454, 4,900,317, 4,909,803 (Reissued as U.S. RE34920), U.S. Pat. Nos. 5,085,654, 5,492,751, 6,476,288 and SIR H1630.

Additionally, an absorbent article of the present invention may include one or more second cuffs that also provide improved containment of liquids and other body exudates. Second cuffs may also be referred to as barrier leg cuffs, inner leg cuffs or "stand-up" elasticized flaps. U.S. Pat. Nos. 4,808,178 and 4,909,803 (Reissued as U.S. RE34920) describe disposable diapers having "stand-up" elasticized flaps that improve the containment of the leg regions.

First cuff and second cuff may both be provided by way of a dual cuff, as exampled in U.S. Pat. Nos. 4,695,278 and 4,795,454. Additional cuffs may be provided in an article of the present invention as detailed in US Statutory Invention Registration H1630.

The backsheet 12 may or may not be impervious to fluids (e.g., menses, urine, and/or runny feces). Accordingly, one embodiment of the backsheet is manufactured from a thin plastic film, although other flexible liquid impervious or pervious materials may also be used. As used herein, the term "flexible" refers to materials which are compliant and will readily conform to the general shape and contours of the human body. The backsheet 12 prevents the exudates absorbed and contained in the absorbent core from wetting articles which contact the absorbent article such as bedsheets, pants, pajamas and undergarments. The backsheet 12 may thus comprise a woven or nonwoven material, polymeric films such as thermoplastic films of polyethylene or polypropylene, and/or composite materials such as a film-coated nonwoven material (i.e., having an inner film layer and an outer nonwoven layer). A suitable backsheet 12 is a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 12 is preferably embossed and/or matte-finished to provide a more clothlike appearance. Further, the backsheet 12 may permit vapors to escape from the absorbent core (i.e., the backsheet is breathable) while still preventing exudates from passing through the backsheet. The size of the backsheet 12 is dictated by the size of the absorbent core 18 and the exact absorbent article design selected.

The backsheet 12 and the topsheet 10 are positioned adjacent a garment facing surface and a wearing facing surface, respectively, of the absorbent core. The absorbent core 18 is preferably joined with the topsheet 10, the backsheet 12, or both in any manner as is known by attachment means such as those well known in the art. However, embodiments of the present invention are envisioned wherein portions of the entire absorbent core are unattached to one or both of the topsheet 10 and the backsheet 12.

For example, the backsheet 12 and/or the topsheet 10 may be secured to the absorbent core 18 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986. An exemplary attachment means of an open pattern network of filaments comprises several lines of adhesive filaments swirled into a spiral pattern such as illustrated by the apparatus and method shown in U.S. Pat. Nos. 3,911,173, 4,785,996 and 4,842,666. Alternatively, the attachment means may comprise heat bonds, pressure bonds, ultrasonic bonds, dynamic mechanical bonds, or any other suitable attachment means or combinations of these attachment means as are known in the art.

The backsheet 12 preferably includes an inner and outer layer, each of which can be bonded to the other by a variety of means known in the art, including thermal bonds, adhesive bonds, ultrasonic lamination, or the like. Adhesive bonding can also be accomplished using adhesive slot coating, high frequency oscillation patterns, for example in swirl or spray patterns, and other fine denier and/or high coverage application techniques. Suitable laminate adhesives, which can be applied continuously or intermittently, can be obtained from Findley Adhesives, Inc. or from National Starch and Chemical Company.

The outer layer (or outer cover) of the backsheet can be made in a variety of forms using different processes. For example, the outer layer may be formed as a carded web, a bonded carded web, a spunbond web, a needled fabric, a woven fabric, or the like to provide a generally cloth-like texture to the wearer. Other additives such as titanium dioxide can represent about 0.5% or less, particularly about 0.3% or less, of the outer layer. In one particular embodiment, the outer layer comprises a spunbond web formed of about 99.5 to 100% polypropylene resin and about 0.5% or less other additives. The outer layer is desirably a lightweight material having a basis weight of about 15 to about 30 gsm and more preferably from about 15 to about 25 gsm.

The articles of the present invention additionally comprise one or more absorbent cores 18. The absorbent core 18 is at least partially disposed between the topsheet 10 and the backsheet 12 and may take on any size or shape that is compatible with the disposable absorbent article. Exemplary absorbent structures for use as the absorbent core of the present invention that have achieved wide acceptance and commercial success are described in U.S. Pat. Nos. 4,610,678, 4,673,402, and 4,888,231, and 4,834,735. The absorbent core may further comprise the dual core system containing an acquisition/distribution core of chemically stiffened fibers positioned over an absorbent storage core as detailed in U.S. Pat. Nos. 5,234,423 and 5,147,345.

In general, the absorbent core 18 is capable of absorbing or retaining liquids (e.g., menses, urine, and/or other body exudates). The absorbent core 18 is preferably compressible, conformable, and non-irritating to the wearer's skin. The absorbent core 18 may be manufactured in a wide variety of sizes and shapes (e.g., rectangular, oval, hourglass, "T" shaped, dog bone, asymmetric, etc.). The absorbent core 18 may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

As discussed herein "absorbent gelling materials" and "superabsorbent polymers" are those materials that, upon contact with aqueous fluids, such as bodily fluids, imbibes such fluids and form hydrogels. These absorbent gelling materials are typically capable of absorbing large quantities of aqueous bodily fluids, and further capable of retaining such absorbed fluids under moderate pressures. These absorbent gelling materials are typically in the form of discrete, nonfibrous particles. Other forms, such as fibers, foams, sheets, strips, or other macrostructures, are also suitable for use herein. Suitable absorbent gelling materials in the form of open cell foams may include those disclosed in U.S. Pat. Nos. 3,563,243, 4,554,297, 4,740,520, and 5,260,345.

The configuration and construction of the absorbent core 18 may also be varied (e.g., the absorbent core may have varying caliper zones and/or have a profile so as to be thicker in the center; hydrophilic gradients; superabsorbent gradients; or lower average density and lower average basis weight zones, e.g., acquisition zones; or may comprise one or more layers or structures). The total absorbent capacity of the absorbent core 18 should, however, be compatible with the design loading and the intended use of the absorbent article. Further, the size and absorbent capacity of the absorbent core may be varied to accommodate different uses such as diapers, incontinence pads, pantiliners, regular sanitary napkins, and overnight sanitary napkins, and to accommodate wearers ranging from infants to adults. The absorbent core 18 can include other absorbent components that are often used in absorbent articles, for example, a dusting layer, a wicking or acquisition layer, or a secondary topsheet for increasing the wearer's comfort.

In certain embodiments of the present invention, the absorbent article may also include a sublayer disposed between the topsheet 10 and the backsheet 12. The sublayer may be any material or structure capable of accepting, storing or immobilizing bodily exudates. Thus, the sublayer may include a single material or a number of materials operatively associated with each other. Further, the sublayer may be integral with another element of the absorbent article or may be one or more separate elements joined directly or indirectly with one or more elements of the article. Further, the sublayer may include a structure that is separate from the core or may include or be part of at least a portion of the core.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. Nos. 6,680,422 and 5,941,864. Further, the sublayer, or any portion thereof, may include or be coated with a lotion or other known substances to add, enhance or change the performance or other characteristics of the element.

Absorbent articles suitable for use as the present invention include diapers, training pants, incontinence products, diaper pants, disposable underwear, or the like. Suitable training pants and diaper pants can have seamed side portions or refastenable side portions. The present invention is particularly suited for use with training pants or diaper pants to aid in toilet training Particular diapers and training pants suitable for use with the present invention are disclosed in U.S. Pat. Nos. 3,860,003, 4,636,207, 4,695,278, 4,704,115, 4,795,454, 4,900,317, 4,909,803 (Reissued as U.S. RE34920), U.S. Pat. Nos. 5,085,654, 5,492,751, 6,476,288, 6,627,787, 5,507,760, 5,609,587, 5,635,191, 5,643,588, 6,118,041, SIR H1630, U.S. Pat. Nos. 5,246,433, 5,769,838, 5,899,895, 5,899,896, and 6,120,487. Additional patents discussing suitable training pants are disclosed earlier herein.

The article of the present invention may also comprise an elastic waist feature that provides improved fit and containment; and a fastening system which forms a side closure which maintains the first waist region and the second waist region in an overlapping configuration such that lateral tensions are maintained around the circumference of the absorbent article to maintain the absorbent article on the wearer. The absorbent article may also comprise elasticized side panels (not shown) in the waist regions and to provide an elastically extensible feature that provides a more comfortable and contouring fit and more effective application of the absorbent article. In certain embodiments, the elasticized side panels are positioned such that a front and rear side panel are joined to one another along their longitudinal edges. This joining along the longitudinal edges of the panels may be permanent or refastenable. For permanent joints, the panels may be adhered to one another via ultrasonic bonding, high tack, adhesives, etc. For refastenable joints, the panels may be joined via hook and loop fasters, mild co-adhesive materials, low tack adhesives, etc.

"Sound Pressure Level Test".

The films of the present invention may have a sound pressure level over the frequency octave range of 2000 Hz 6300 Hz of less than about 43 dB, less than about 40 dB. The film is tested using a testing mechanism comprised of a box (shown in FIG. 2) having internal dimensions 192 mm wide by 203 mm deep by 198 mm in height. The box is made out of a rigid material able to hold the weight of the rotational mechanism (shown in FIG. 3) and stand the forces inflicted during testing without deformation. One such suitable material is Lexan with a thickness of 12 mm. The box has an opening at the top surface 401 large enough to allow mounting film samples on the test brackets 411 and allow access to the rotational mechanism for adjustments as needed. The box is mounted on rubber footings 412, one on each corner of the bottom surface of the box. The bottom of the box 410 is closed with a rigid material to provide stability to the box.

Figure 2:
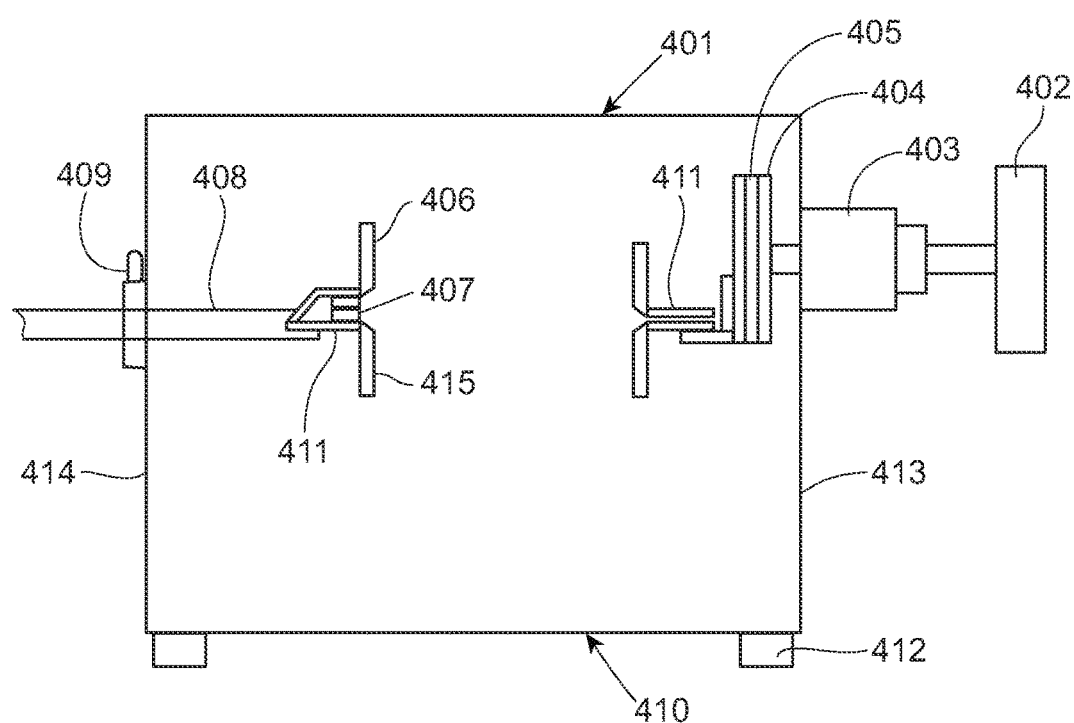
FIG. 2 is a schematic representation of a sound measurement device.
Figure 3:
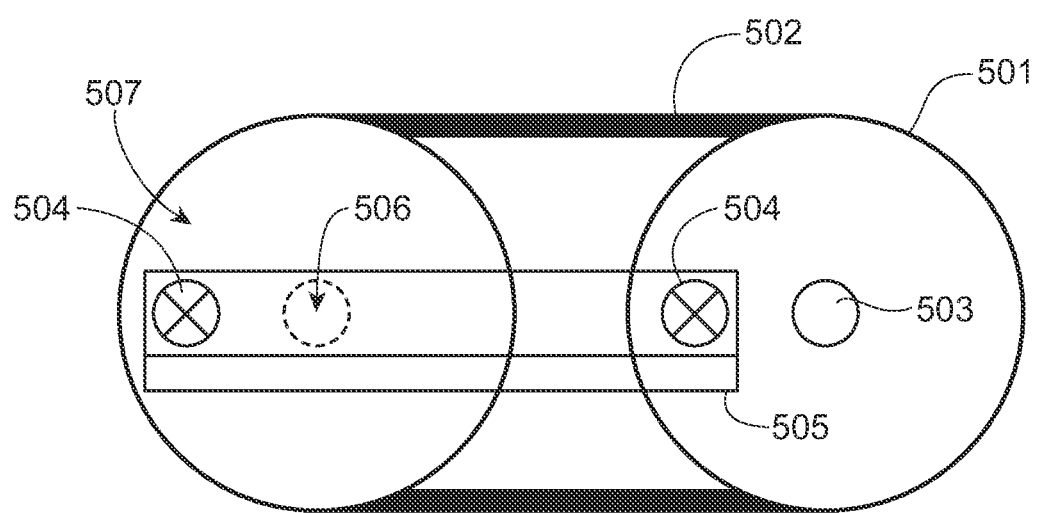
FIG. 3 is a schematic representation of a rotational mechanism of the sound measurement device.

A block with dimensions 13.1 cm long by 2.54 cm deep by 4 cm tall serves at the supporting base 403 of the rotational mechanism and it is attached to the front surface of the box 413. Base 403 is made of Nylon or other similar material. Base 403 supports two pins 503 and 506 on which two nylon pulleys 501 and 507 are free to rotate. The nylon pulleys are 7.5 cm in diameter and are connected by a rubber belt 502 in a way that both pulleys rotate at the same speed when the mechanism is activated. On the opposite end of pin 506, a wheel 402 is attached which is used to operate the mechanism. A side view of the pulley 404 and the belt 405 are shown in FIG. 2 as they are located in the box.

A mounting bracket 505 is attached to both pulleys at attachment point 504. Point 504 is mounted on the pulley at a radial distance of 25 mm from the pin 503 on pulley 501 and at a radial distance of 25 mm from the pin 506 on pulley 507. Attached to the mounting bracket 505 is clamp 411. Clamp 411 is at least 100 mm wide and has rubber pads 407 at the top and bottom of the clamp to properly secure the test sample.

A second clamp identical to clamp 411 is mounted on a rod 408 which is located opposite to the first clamp. The rod 408 goes thru a hole on the back surface of the box 414. The hole contains a locking mechanism 409 which when disengaged allows the clamp 411 to slide towards the back of the box 414 for sample loading and slide towards the clamp mounted to the rotational mechanism for sample testing.

Each clamp 411 has a piece of Lexan 406 with dimensions 100 mm long, 32 mm tall and 1.5 mm thick attached to the top jaw of the clamp. A second piece of Lexan 415 with dimensions 100 mm long, 54 mm tall and 1.5 mm thick is attached to the bottom jaw of the clamp. The means used to affix the plexiglass to the clamp will vary depending on the clamp design selected and are not intended to be prescribed. The attachments must be able to stand the stresses induced during testing.

When the clamp 411 on mounting bracket 505 is moved to its highest vertical position, it will be parallel with clamp 411 mounted on rod 408, but at a vertical distance of 10 mm. Test samples loaded in this position will maintain both ends of the test specimen parallel with each other.

When the mechanism is activated the first clamp 411 on mounting bracket 505 will rotate in a circular path with a 23 mm radius while the second clamp 411 on rod 408 stays stationary. To load a film test specimen of 100 mm×100 mm unlock the locking mechanism 409 to allow the rod 408 to move and set the distance between the first and second clamps 411 to 67 mm. The first clamp on mounting bracket 505 is moved to its highest vertical position and the film test specimen is clamped with one edge in the first clamp and the opposite edge in the second clamp. Once the test specimen is secured in the clamps unlock the locking mechanism 409 and slide back the second clamp 411 mounted on rod 408 and set the distance between clamps to 15 mm. Lock the locking mechanism to prevent the second clamp from moving back.

The box 401 is placed inside an Audiometric test enclosure with a Noise Isolation Class (NIC) equal or higher to 38 as calculated in accordance with Classification ASTM E 413 Test Method E596. The microphone with preamplifier of the sound meter is placed in the test enclosure 50 mm above the second stationary clamp 411 and centered over the test sample. The analyst performing the test steps into the audiometric test chamber with the sound meter and closes the door of the chamber before setting the sound meter instrument to collect data. The analyst turns the wheel of the testing mechanism (402) at a rate of 1 revolution per second for 30 seconds and the sound pressure level is recorded by the sound meter at the ⅓ octave frequency range between 2000 Hz and 6300 Hz. After wards the analyst stops the sound meter data collection and steps out the Audiometric test enclosure. The data from the sound meter is later downloaded to a computer for analysis. It is recommended to select an integrating sound meter which meets the following standards: IEC 61672-1:2002, ANSI S1.4, ANSI S1.4. The sound meter must have data logging software of spectral data and ⅓ octave band frequency analysis.

Embodiments of the film of the present disclosure are tested and compared to a film not having low sound pressure level. All samples produced are made with manually mixed batches of 4000 g. The following resins are used for the trials.

Low Linear Density Polyethylene resin LLDPE LL3402.48 cast hexane polyethylene with a thermal stabilizer additive manufactured by ExxonMobil with a typical resin density of 0.942 g/cm3 and a Melt Index of 2.0 g/10 min may be obtained from test method ASTM D1238 may be tested at 190 C/2.16 Kg and a Peak melting temperature of 128 C as reported in the manufacturer's technical data sheet.

Low Density Polyethylene resin LD105.30 is a homopolymer resin manufactured by ExxonMobil with a 1000 ppm Antiblock content and a thermal stabilizer additive. The typical resin density is 0.923 g/cm3 and Melt Index of 2.0 g/10 min may be obtained from test method ASTM D1238 may be tested at 190 C/2.16 Kg and a Peak melting temperature of 111 C as reported in the manufacturer's technical data sheet.

An olefinic elastomer may be the elastomeric resin. Vistamaxx 6102 Propylene-based elastomer with 16% Ethylene content manufactured by ExxonMobil using ExxonMobil Chemical's EXXPOL catalyst. The typical resin density is 0.862 g/cm3 and Melt Index of 1.5 g/10 min as reported in the manufacturer's technical data sheet.

Titanium Oxide may be one of the particle additives. The Titanium Oxide may be compounded by Ampacet in a masterbatch which is commercially available under the tradename 11748 White PE MB. The carrier resin used in the masterbatch is a Low Linear Density Polyethylene with a Melt Index of 20 per ASTM D1238 190 C/2.16 Kg and a density of 0.92 g/cm3 as reported by the manufacturer. The final concentrate masterbatch may contain 70% Titanium Oxide and may be compounded targeting a Melt Index Specification range of 13-23 per ASTM D1238 190 C/2.16 Kg.

Calcium Carbonate may be one of the particle additives. The Calcium Carbonate may be compounded by Ampacet. A commercially available masterbatch may be tested, tradename 1000175-N CaCO3 PE MB with CaCO3 average particle size of 0.8 micron. The carrier resin used in the masterbatches was a Low Linear Density Polyethylene with a Melt Index of 20 per ASTM D1238 190 C/2.16 Kg and a density of 0.92 g/cm3 as reported by the manufacturer.

Examples 1-3 may be produced in a Davis Standard small scale cast extrusion line equipped with a 2.54 cm diameter single screw extruder with 3 temperature zones and a 25.4 cm monolayer cast extrusion die. The screw speed may be set to 60 RPM for Examples 1 and 2 and 45 RPM for Example 3. The temperatures at the extrusion line may be maintained at the following set points below. The pull roll may be chilled to about 18° C. and the roll used may be a smooth roll.

| Zone | Temperature Set point for Example 1 and 2 (° C.) | Temperature Set point for Example 3 (° C.) |
|---|---|---|
| 1 | 190 | 200 |
| 2 | 200 | 230 |
| 3 | 210 | 230 |
| Clamp | 220 | 230 |
| Hose | 225 | 230 |
| Die | 230 | 230 |

| Example | LLDPE 3402.48 grams | LDPE 105.30 grams | Vistamaxx 6102 grams | 1000175-N CaCO3 PE MB grams | 11748 White PE MB grams | Basis weight (g/m2) |
|---|---|---|---|---|---|---|
| 1 | 900 | 800 | 0 | 2300 | 0 | 17.33 |
| 2 | 800 | 800 | 400 | 1600 | 400 | 13.53 |
| 3 | 750 | 800 | 120 | 2130 | 200 | 16.68 |

The examples described above may be tested to determine a sound pressure level using by the Sound Pressure Level Test herein.

The Particle % weight contained in a 4000 grams batch of resin mix was calculated using the following formula:

Particle % weight=[(grams of master batch 1×percent particle content on master batch 1)+(grams of master batch 2×percent particle content on master batch 2)]/4000 grams The Polyolefin % weight contained in a 4000 grams batch of resin mix was calculated using the following formula:

Polyolefin % weight=(grams of resin 1+grams of resin 2)/4000 grams

The film examples are incrementally stretched by passing them between intermesh rollers that stretch the films as the film pass between the rollers. The intermesh rollers have teeth with a spacing of 1.52 mm. This spacing is known as the pitch of the tooling. The depth of engagement between the top and bottom intermeshing rolls can be measured as the vertical distance from the top of the tooth on the top roll to the top of the tooth on the bottom roll next to it. The rollers are mounted on a frame and connected by gears in such way that both the top and bottom rollers rotate at the same speed. The pieces of film are manually fed between the rollers which are turned manually to incrementally stretch the film.

| Example | Particle % weight | Particle | Polyolefin % weight | Elastomeric resin % weight | 1.52 mm pitch tooing depth of engagement (mm) | Average SPL (dB) 2000-6300 Hz |
|---|---|---|---|---|---|---|
| 1 | 35 | CaCO3 | 65 | 0 | 0 | 43.3 |
| 1a | 35 | CaCO3 | 65 | 0 | 0.508 | 36.2 |
| 1b | 35 | CaCO3 | 65 | 0 | 0.889 | 29.8 |
| 2 | 31 | Blend of CaCO3/TiO2 | 59 | 10 | 0.000 | 38.2 |
| 2a | 31 | Blend of CaCO3/TiO2 | 59 | 10 | 0.635 | 33.0 |
| 2b | 31 | Blend of CaCO3/TiO2 | 59 | 10 | 0.762 | 31.7 |
| 3 | 35 | Blend of CaCO3/TiO2 | 62 | 3 | 0.000 | 48.7 |
| 3a | 35 | Blend of CaCO3/TiO2 | 62 | 3 | 0.762 | 39.5 |
| 3b | 35 | Blend of CaCO3/TiO2 | 62 | 3 | 0.889 | 32.2 |
| 3c | 35 | Blend of CaCO3/TiO2 | 62 | 3 | 1.016 | 28.5 |

With increasing depth of engagement, the film is incrementally stretched and thinned out creating bands of thinner film. With this process, the young's modulus of the film is decreased in the direction the film was incrementally stretched and therefore the noise produced by the film is decreased.

Various tooling pitch and the depth of engagement between the top and bottom intermeshing rolls can provide the same incremental stretching by applying in the stretched area the same engineering strain. Engineering strain is the ratio between the amount of deformation locally experienced by the film and the original width of the area being incrementally stretched.

| 1.52 mm pitch tooling Depth of Engagement (mm) | Calculated Engineering Strain |
|---|---|
| 0.508 | 20% |
| 0.635 | 30% |
| 0.762 | 41% |
| 0.889 | 54% |
| 1.016 | 67% |

The calculated Engineering Strain is calculated using the following formula:

Calculated Engineering Strain=[Stretched length–(tooling Pitch/2)]/(tooling pitch/2);

where Stretched length=square root [(tooling pitch/2)^2+ (depth of engagement)^2].

Actual strains may be higher as it is known that the tooth geometry and material and process of manufacturing of the intermeshing rolls may affect the final strain experienced.

As evidenced in the data above, a film comprising: from about 20 wt. % to about 85 wt. % of a polyolefin component and from about 20 wt. % to about 45 wt. % of a particle component, the film having a basis weight of from about 5 gsm to about 25 gsm, wherein the film is activated and subjected to an engineering strain of greater than about 20%; results the film having a sound pressure level of less than about 43 dB as determined by the Sound Pressure Level Test herein.

For comparison, the sound pressure level of some currently marketed films was tested, and the ones tested did not have a sound pressure level of less than about 43 dB as determined by the Sound Pressure Level Test herein. A film used in the production of LUVS diapers manufactured by Procter and Gamble produced in March 2012 has an average sound pressure level of 47.9 dB; a film used in the production of Pampers Baby Dry Diapers manufactured by Procter and Gamble in February 2014 has an average sound pressure level of 46.2 dB; a film used in the production of wrappers for sanitary napkins manufactured by Procter and Gamble produced in March 2012 has an average sound pressure level of 46.5 dB; a film from GOON premium size 2 diapers production Lot number 923212302 has an average sound pressure level of 45.3 dB. The film was removed from the diaper by dissolving the adhesive gluing the film to the core and nonwoven soft cover with a solvent.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A film comprising:
   a. from about 20 wt. % to about 85 wt. % of a polyolefin component; and
   b. from about 20 wt. % to about 45 wt. % of a particle component;
   wherein the film has a basis weight of from about 5 gsm to about 25 gsm prior to activation;
   wherein the film is activated and subjected to an engineering strain of greater than about 20%;

wherein the film has a sound pressure level of less than about 43 dB according to the Sound Pressure Level Test described herein.

2. The film of claim 1, wherein the basis weight is from about 13 gsm to about 20 gsm.

3. The film of claim 1, wherein the polyolefin component is selected from the group consisting of linear low density polyethylene polymers, low density polyethylene polymers, high density polyethylene polymers, polypropylene polymers, and mixtures thereof.

4. The film of claim 1, wherein the polyolefin component is selected from the group consisting of linear low density polyethylene polymers and low density polyethylene polymers.

5. The film of claim 1, wherein the polyolefin component has a density of from about 0.91 g/cm$^3$ to about 0.95 g/cm$^3$.

6. The film of claim 1, comprising from about 1 wt. % to about 30 wt. % of an elastomeric resin.

7. The film of claim 1, comprising less than about 15 wt. % of an elastomeric resin.

8. The film of claim 7, wherein the elastomeric resin is selected from the group consisting of propylene based elastomer, propylene ethylene copolymer, and styrenic block copolymer resin.

9. The film of claim 7, wherein the elastomeric resin is a propylene based elastomer.

10. The film of claim 7, wherein the elastomeric resin has a degree of crystallinity or end block content of from about 5% to about 33%.

11. The film of claim 1, comprising from about 25 wt. % to about 40 wt. % of the particle component.

12. The film of claim 1, wherein the particle component is selected from the group consisting of friction reducing particles and opacifier particles.

13. The film of claim 1, wherein the particle component is selected from the group consisting of CaCO3, TiO2, and combinations thereof.

14. The film of claim 1, wherein the particle component has a density of from about 1.8 g/cm$^3$ to about 4.5 g/cm$^3$.

15. The film of claim 1, wherein the particle component has a density of at least about 2 times the density of the polyolefin component.

16. The film of claim 1, wherein the film is activated with a 1.52 mm pitch tooling such that the depth of engagement of the tooling is from about 0.508 mm to about 1.27 mm.

17. The film of claim 1, wherein the film is subjected to an engineering strain of from about 20% to about 70%.

18. The film of claim 1, wherein the film has a sound pressure level of less than about 40 dB according to the Sound Pressure Level Test described herein.

19. The film of claim 1, wherein the film is incorporated in an absorbent article selected from the group consisting of a diaper, a pant, an absorbent insert for a diaper or pant, a sanitary napkin, and a pantiliner.

20. The film of claim 1, wherein the film is incorporated in a package or wrapper.

21. The film of claim 1, wherein the film is incorporated in a component of an absorbent article selected from the group consisting of a backsheet, a waistband, fastening members, and ears.

22. The film of claim 1, wherein the film is activated using a depth of engagement of 0.5 or greater.

23. A film comprising:
   a. from about 20 wt. % to about 85 wt. % of a polyolefin component;
   b. less than about 15 wt. % of an elastomeric resin; and
   c. from about 20 wt. % to about 45 wt. % of a particle component;
   wherein the film has a basis weight of from about 5 gsm to about 25 gsm prior to activation;
   wherein the film is activated and subjected to an engineering strain of from about 24% to about 85%; and
   wherein the film has a sound pressure level of less than about 40 dB according to the Sound Pressure Level Test described herein.

* * * * *